US012746312B2

(12) United States Patent
Post et al.

(10) Patent No.: US 12,746,312 B2
(45) Date of Patent: Sep. 29, 2026

(54) BREAST PUMP FLANGE ASSEMBLY AND METHOD OF USE

(71) Applicants: Marcella Lee Post, Edmond, OK (US); Tina Louise Michael-Shine, St. Charles, MO (US)

(72) Inventors: Marcella Lee Post, Edmond, OK (US); Tina Louise Michael-Shine, St. Charles, MO (US)

( * ) Notice: Subject to any disclaimer, the term of this patent is extended or adjusted under 35 U.S.C. 154(b) by 290 days.

(21) Appl. No.: 18/406,357

(22) Filed: Jan. 8, 2024

(65) Prior Publication Data

US 2024/0139389 A1 May 2, 2024

Related U.S. Application Data

(63) Continuation-in-part of application No. 16/794,833, filed on Feb. 19, 2020, now Pat. No. 11,931,491.

(51) Int. Cl.
*A61M 1/06* (2006.01)

(52) U.S. Cl.
CPC ........ *A61M 1/06935* (2021.05); *A61M 1/066* (2014.02); *A61M 1/0697* (2021.05)

(58) Field of Classification Search
CPC ....... A61M 1/066; A61M 1/064; A61J 113/00
See application file for complete search history.

(56) References Cited

U.S. PATENT DOCUMENTS

| | | | |
|---|---|---|---|
| 5,100,406 A | 3/1992 | Panchula | |
| 5,885,246 A | 3/1999 | Ford | |
| 6,383,164 B1 | 5/2002 | Johansen et al. | |
| 6,663,587 B2 | 12/2003 | Silver et al. | |
| 7,354,418 B2 | 4/2008 | Lee et al. | |
| 7,776,009 B2 | 8/2010 | Renz et al. | |
| 7,875,000 B2 | 1/2011 | Krebs et al. | |
| 7,972,297 B2 | 7/2011 | Bryan et al. | |
| 8,052,635 B1 | 11/2011 | Kelly et al. | |
| 8,523,804 B2 | 9/2013 | Cudworth | |
| 9,248,223 B2 | 2/2016 | Van Der Kamp et al. | |
| 2002/0198489 A1* | 12/2002 | Silver | A61M 1/064 119/14.47 |

OTHER PUBLICATIONS

Breast Pump Flanges, Lansinoh, Feb. 10, 2020.
Personal Fit Breastshields, Medela Feb. 10, 2020.

* cited by examiner

*Primary Examiner* — Courtney Fredrickson
(74) *Attorney, Agent, or Firm* — D. Ward Hobson

(57) ABSTRACT

An improved breast pump flange assembly, flexible membrane and method of use are disclosed. In some embodiments, the breast pump flange assembly includes a flanged housing having an interior chamber extending therethrough. The flanged housing including an upper receiving portion having a first diameter, a substantially tubular middle portion having a second diameter, and a substantially tubular lower connecting portion having a third diameter. In some embodiments, the breast pump flange assembly further includes a flexible membrane having an opening extending therethrough. The flexible membrane having one or more support pad positioned at least partially around the opening of the tubular middle portion of the flanged housing. The support pad configured to simulate the sensation of a baby's mouth on a breast, causing the breast to be massaged by intermittent suction action produced by a breast pump.

8 Claims, 4 Drawing Sheets

200

BREAST PUMP FLANGE ASSEMBLY AND METHOD OF USE

CROSS REFERENCE TO RELATED APPLICATIONS

This application is a continuation-in-part of U.S. application Ser. No. 16/794,833 filed on Feb. 19, 2020, which is expressly incorporated herein by reference in its entirety.

FIELD OF INVENTION

The invention is in the technical field of breast pumps, breast pump flanges and flexible inserts for use with breast pump flanges. In particular, the invention is generally directed to a novel breast pump flange, flange assembly, flexible membrane and method of use as described and claimed herein.

BACKGROUND

Traditional breast pump flanges, sometimes referred to as "breast shields" are known in the art and are commercially available. For example, the "Comfort Fit" Flange offered by Lansinoh® and the "Personal Fit" Breast Shield offered by Medela®. Traditional breast pump flanges are often constructed from plastic and generally have a large cone-shaped portion where the breast is inserted and a smaller tube-shaped portion where the nipple is pulled through when the flange is attached to a breast pump. The cone-shaped portion fits directly over a user's breast and nipple to form a seal. The seal creates a vacuum that draws the nipple into the tube-shaped portion for milk extraction when the flange is connected to a breast pump, such as a hand-held breast pump or automatic breast pump, for example.

Because the nipple is pulled from the larger cone-shaped portion into the smaller tube-shaped portion of a traditional flange, the area of the flange where the cone narrows and connects to the tube is typically the area of greatest friction and user discomfort. Problems associated with such traditional breast pump flanges include generally, but are not limited to, for example, breast pain, blocked or clogged ducts, soreness, dryness, engorgement and breast infections. Such problems are often compounded in real life, due to exhaustion, anxiety, fatigue, and other issues commonly associated with new mothers, new-born babies and breast milk production.

To improve the comfort, safety and efficiency of traditional breast pump flanges, it would be advantageous to provide an improved breast pump flange assembly, flexible membrane and method of use as disclosed and claimed herein. The improved breast pump flange assembly and flexible membrane may also include one or more soft flexible pillow or support pad positioned at least partially around the opening of the tube-shaped portion where user discomfort is greatest. Each support pad is configured to simulate the movement and sensation of a baby's mouth on a breast, causing the breast to be massaged by the intermittent suction action produced when the flange is attached to a breast pump. The support pads are configured to be modifiable in that they can each be selectively connected, attached, or detached to or from the flexible membrane, in any number of positions, configurations or orientations on the flexible membrane, by the user at home on the fly and in real time, to create any number of custom fits and/or so that the support pads can be selectively arranged, connected, removed, washed, and then selectively reconnected to the flexible membrane in any orientation or position and for further use. The massaging pressure produced by the support pad, which is applied to the mammary ducts of the breast, significantly increases user comfort, health and breast milk productivity. Thus, providing significant advantages over traditional breast pump flanges and breast shields.

SUMMARY OF THE INVENTION

In some embodiments, the improved flexible membrane is configured to fit into an existing traditional breast pump flange and be used with an existing traditional breast pump. While in other embodiments, the improved flexible membrane is configured to be used with the improved flanged housing described and claimed herein to form an improved flange assembly. The improved breast pump flange assembly generally includes a flanged housing having an interior chamber extending therethrough. The flanged housing having an upper receiving portion having a first diameter, a substantially tubular middle portion having a second diameter, and a substantially tubular lower portion having a third diameter. The upper receiving portion of the flanged housing configured for receiving a nipple of a user. The breast pump flange assembly also includes a flexible membrane. The flexible membrane generally includes an outer portion, a middle portion, an inner portion, and an opening extending therethrough. Wherein the inner portion contains a support pad positioned at least partially around the opening of the flexible membrane. The support pad configured to simulate the sensation of a baby's mouth on a user's breast by causing the breast to be massaged by intermittent suction action produced by a breast pump. Wherein the support pad applies pressure to the mammary ducts of the breast increasing user comfort and breast milk productivity.

The support pad is positioned at least partially around the mouth of the opening at the tube-shaped middle portion of the flanged housing, the area of greatest user discomfort. The support pad simulates the action of a baby's mouth on the breast when the flange assembly is connected to a breast pump. In some embodiments the support pad is positioned completely around the opening, while in other embodiments, the support pad may be positioned partially around the opening, while in other embodiments there may be more than one support pad, with each support pad positioned at a different location around the opening. For example, in some embodiments, one support pad may be positioned around an upper portion of the opening while a second support pad may be positioned around a lower portion of the opening. In this embodiment, no support pad is found around the sides of the opening, so as to mimic the sensation of a baby's mouth on a user's breast.

The configuration, position and number of support pads may be modified, increased or decreased to accommodate a variety of different sized and shaped women and to provide maximum comfort and versatility. For example, the support pads are configured to be modifiable in that they can each be selectively connected, attached, or detached to or from the flexible membrane, in any number of positions, configurations or orientations on the flexible membrane, by the user at home on the fly and in real time, to create any number of custom fits and/or so that the support pads can be selectively removed, washed, and then selectively reconnected or attached to the flexible membrane for further use as desired. For example, a user may selectively attach one support pad to the flexible membrane, and later desire to change the fit and add a second or third support pad to the flexible membrane, or the user may rearrange the location or position of the support pads connected to the flexible membrane for additional or different support and comfort. Each support pad may be selectively attached, connected, and detached to the flexible membrane by a user by any connection means known in the art, including but not limited to, adhesives, including pressure and heat sensitive adhesives, chemical bonding, latches, structural grooves, ridges, ribs, locking mechanisms, pins, bolts, screws, flanges, and other connecting means known in the art. It should be understood, that in some embodiments, the flexible membrane may have no support pads, while in other embodiments, the flexible membrane may have one, two, or three or more support pads connected thereto, for example. The position, configuration, and orientation of the support pads on the flexible membrane is capable of being rearranged and detachably connected and removed from the flexible membrane, in any orientation or position, for maximum comfort and so that the support pads and the flexible membrane may be used with a variety of different sized and shaped women without having to purchase more or different sized or shaped traditional breast pump equipment. Thereby, providing significant advantages over traditional breast pump equipment. Each support pad, which may be formed from or contain a soft, flexible solid, liquid, semi-liquid, or gel, including silicone for example, provides soft contact around the circumference of the areola to the nipple and applies consistent pressure to the mammary ducts of the breast. Utilizing the intermittent suction action of the breast pump, the support pad causes the breast and nipple to be massaged during the suction process creating a more natural sensation (like a baby sucking) on the breast. This facilitates breast feeding by increasing comfort and productivity in producing breast milk while pumping.

The improved breast pump flange assembly, flexible membrane and method of use induces a natural milk letdown reflex with the expression of breast milk and thereby creates a more comfortable experience for the user. Comfort and increased milk production are two major advantages of the improved breast pump flange assembly, flexible membrane and method of use compared to traditional breast pump flanges. The improved breast pump flange assembly, flexible membrane and method of use are also easier and more comfortable to use than traditional breast pump flanges, thereby encouraging women to pump more, breastfeed longer, empty their mammary glands (preventing common mastitis caused by ducts being plugged), and decreasing chaffing and friction during pumping. This offers significant health benefits to the mother and baby, reduces medical expenses and limits the cost of formula supplementation. In addition, because the flexible membrane may be inserted into, adhered to, or detachably connected to an existing flange or the flanged housing described herein, the flexible membrane may be cleaned and re-used or alternatively, thrown-away and a new flexible membrane used therewith. Thereby increasing the versatility, cleanliness and cost-effectiveness of the improved flange assembly and flexible membrane and providing significant advantages over traditional breast pump flanges.

In some embodiments, the housing of the breast pump flange assembly may be constructed from a nylon material that is bisphenol A "BPA" free and dishwasher safe. Further, in some embodiments, the housing of the breast pump flange assembly may contain a smooth and continuous support pad constructed from, or filled with, silicone such that the support pad is capable of movement sufficient to massage the breast when connected to a breast pump. Embodiments of the inventive concepts disclosed and claimed herein are also configured to be used as a replacement breast pump flange or alternatively, as a reusable or discard-able insert designed to be used with a traditional breast pump flange. The inventive concepts disclosed herein are configured to facilitate breastfeeding while alleviating the friction and soreness often caused by use of traditional breast pump flanges.

In some embodiments, the improved breast pump flange assembly includes a flanged housing having an interior chamber extending therethrough. The flanged housing including an upper receiving portion having a first diameter, a substantially tubular middle portion having a second diameter, and a substantially tubular lower portion having a third diameter. The upper receiving portion of the flanged housing including an opening configured for receiving a breast and nipple of a user. The middle portion for pulling the nipple therethrough during the suction process. The lower portion of the flanged housing for connecting the flanged housing to a breast pump so that breast milk may flow therethrough.

In some embodiments, the breast pump flange assembly further includes a flexible membrane having an opening extending therethrough. The flexible membrane detachably connected to a portion of the interior chamber of the rigid flanged housing. In some embodiments, the flexible membrane may be selectively adhered to the interior of the housing by means of an adhesive and peeled off after use and discarded, for example. The flexible membrane having a support pad positioned around the opening of the flexible membrane and positioned around the opening at the mouth of the middle portion of the flanged housing. The support pad is configured to simulate the sensation of a baby's mouth on a breast, causing the breast to be massaged by intermittent suction action produced by a breast pump, wherein pressure is applied to the mammary ducts of the breast increasing comfort and breast milk productivity.

It is to such an improved flange assembly, flexible membrane, and methods of use thereof that exemplary embodiments of the inventive concepts disclosed and claimed herein are directed.

BRIEF DESCRIPTION OF THE SEVERAL VIEWS OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, drawings, and appendices. In the drawings.

DETAILED DESCRIPTION OF EXEMPLARY EMBODIMENTS

Figure 1:
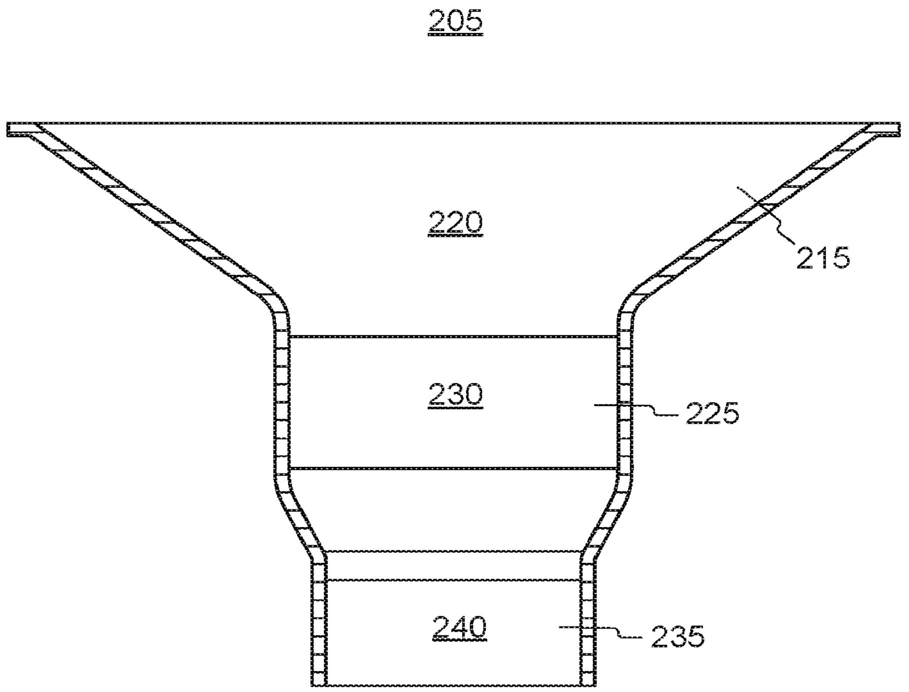
FIG. 1 is a side sectional view of an exemplary embodiment of a flanged housing (205) of a breast pump flange assembly (200) in accordance with the inventive concepts disclosed herein.

Before explaining at least one embodiment of the inventive concepts disclosed herein in detail, it is to be understood that the inventive concepts are not limited in their application to the details of construction and the arrangements of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein, the terms "comprises," "comprising," "Includes," "including," "has," "having," or any other variation thereof, are intended to cover a non-exclusive inclusion. For example, a system, assembly, method, process, article, or apparatus that comprises a list of elements or steps is not necessarily limited to only those elements or steps but may include other elements and steps not expressly listed.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to FIG. 1, shown therein is a side sectional view of an exemplary embodiment of a flanged housing (205) of a breast pump flange assembly (200) in accordance with the inventive concepts disclosed herein. The breast pump flange assembly (200) includes a flanged housing (205) having an interior chamber (210) extending therethrough. The flanged housing (205) having an upper receiving portion (215) having a first diameter (220), a substantially tubular middle portion (225) having a second diameter (230), and a substantially tubular lower portion (235) having a third diameter (240). The upper receiving portion (215) of the flanged housing (205) is configured for receiving a nipple of a user. The breast pump flange assembly (200) further including a flexible membrane (100). The flexible membrane (100) including an outer portion (105), a middle portion (110), an inner portion (115), and an opening (120) extending therethrough. Wherein the inner portion (115) contains a support pad (130) positioned around the opening (120) of the flexible membrane (100). The support pad (130) configured to simulate the sensation of a baby's mouth on a user's breast by causing the breast to be massaged by intermittent suction action produced by a breast pump (209). Wherein the support pad (130) applies pressure to the mammary ducts of the breast increasing user comfort and breast milk productivity.

The flanged housing (205) is shown as having an interior chamber (210) extending therethrough. The interior chamber (210) of the flanged housing (205) is configured for receiving a nipple of a user and permitting breast milk to flow therethrough. In some embodiments, the interior chamber (210) has a diameter of approximately 3.336 inches at the mouth of the upper receiving portion (215), which narrows to a diameter of approximately 1.310 inches at the mouth of the tubular middle portion (225), which narrows to a diameter of approximately 1.00 inch at the mouth of the substantially tubular lower portion (235). It should be understood however, that the diameter of the interior chamber (210) may be any size and may be a variety of different sizes, to comfortably fit a variety of different sized and shaped women and sufficient to function as described and claimed herein.

The flanged housing (205) further includes an upper receiving portion (215) having a first diameter (220). The first diameter (220) of the upper receiving portion being sized for receiving a portion of a breast and nipple of a user. In some embodiments, the first diameter (220) is approximately 3.5 inches, while in other embodiments the first diameter (220) may be greater than 3.5 inches or less than 3.5 inches for example. It being understood that the first diameter (220) may be any size and may be a variety of different sizes, to comfortably fit a variety of different sized and shaped women and sufficient to function as described and claimed herein.

Further, in some embodiments the angle of the upper receiving portion (215) is approximately 105 degrees, while in other embodiments the angle of the upper receiving portion (215) may be greater than or less than 105 degrees. It being understood that the angle of the upper receiving portion (215) may be varied to fit a variety of different sized and different shaped women and to maximize user comfort. The upper receiving portion (215) may be detachably connected to the tubular middle portion (225) which may be detachably connected to the substantially tubular lower portion (235) in some embodiments. While in other embodiments, the upper receiving portion (215), tubular middle portion (225) and substantially tubular lower portion (235) may be formed from a single unitary piece of material, for example.

The flanged housing (205) further includes a substantially tubular middle portion (225) having a second diameter (230). In some embodiments the second diameter (230) of the middle portion (225) is approximately 1.310 inches, while in other embodiments the second diameter (230) may be greater than or less than 1.310 inches, for example. It being understood that the second diameter (230) may be varied to fit a variety of different sized and different shaped women and to maximize user comfort. Further, the upper receiving portion (215) may be detachably connected to the tubular middle portion (225) which may be detachably connected to the substantially tubular lower portion (235) in some embodiments. While in other embodiments, the upper receiving portion (215), tubular middle portion (225) and substantially tubular lower portion (235) may be formed from a single unitary piece of material, for example.

The second diameter (230) of the tubular middle portion (225) is less than the first diameter (220) of the upper receiving portion. The first diameter (220) of the upper receiving portion (215) being sized for receiving a portion of a breast and nipple of a user. As the first diameter (220) of the upper receiving portion (215) narrows at the mouth of the tubular middle portion (225), the upper receiving portion (215) fits directly over a user's breast and nipple to form a seal. The seal creates a vacuum that draws the nipple into the tubular middle portion (225) for milk extraction when the flange is connected to a breast pump.

The flanged housing (205) further includes a substantially tubular lower portion (235) having a third diameter (240). The third diameter (240) of the lower portion (235) is less than the first diameter (220) of the upper receiving portion and less than the second diameter (230) of the middle portion (225). The third diameter (240) of the lower portion (235) being sized for being detachably connected to a breast pump. The first diameter (220) of the upper receiving portion (215) narrows at the mouth of the tubular middle portion (225) and then the second diameter (230) narrows at the mouth of the lower portion (235) to create a seal. The seal creates a vacuum that draws the nipple into the tubular middle portion (225) for milk extraction when the flanged housing (205) is connected to a breast pump.

As described above, the flanged housing (205) may be constructed from a unitary piece of material or alternatively may be detachably connected from a variety of component parts. The flanged housing (205), including each of its component parts, may be constructed from any type of material that is sufficient to function as described and claimed herein. For example, the flanged housing (205) may be constructed from paper, plastics, nylon, silicone, metals, non-metals, alloys, resins, composite materials, organic compounds, non-organic compounds, fabrics, combinations thereof and the like. In some embodiments, the flanged housing (205) may have a thickness of approximately 0.050 inches. While in other embodiments, the flanged housing (205) may have a thickness greater than 0.050 inches, or in other embodiments the flanged housing (205) may have a thickness of less than 0.050 inches for example. However, the flanged housing (205) may be configured in a variety of dimensions to fit various sized and shaped breasts, including but not limited to configurations that are ergonomically designed to maximize comfort, for example.

Further in some embodiments, the flanged housing (205) may also include reinforcing or bracing structures such as struts, ribs, braces, rods or any other suitable reinforcing or bracing structure, or combinations thereof. The shape of the flanged housing (205) is shown as having a cone or circular shaped upper portion and a smaller funnel or tubular shaped middle portion (225) and lower portion (235). However, it should be understood, that the shape of the flanged housing (205) may be configured to have any desired shape, including but not limited to, a circular, triangular, square or any other desired shape sufficient to permit the flanged housing (205) to function as described herein.

Figure 2:
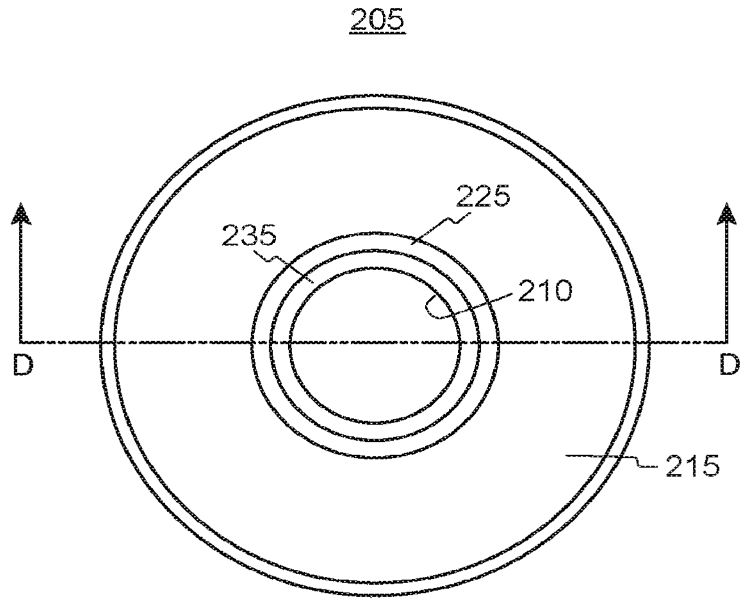
FIG. 2 is a top view of an exemplary embodiment of a flanged housing (205) of a breast pump flange assembly (200) in accordance with the inventive concepts disclosed herein.

Referring now to FIG. 2, shown therein is a top view of an exemplary embodiment of a flanged housing (205) of a breast pump flange assembly (200) in accordance with the inventive concepts disclosed herein. As shown therein, the flanged housing (205) has an interior chamber (210) extending therethrough. The interior chamber (210) of the flanged housing (205) is configured for receiving a nipple of a user and permitting breast milk to flow therethrough. In some embodiments, the interior chamber (210) has a diameter of approximately 3.336 inches at the mouth of the upper receiving portion (215), which narrows to a diameter of approximately 1.310 inches at the mouth of the tubular middle portion (225), which narrows to a diameter of approximately 1.00 inch at the mouth of the substantially tubular lower portion (235). It should be understood however, that the diameter of the interior chamber (210) may be any size and may be a variety of different sizes, to comfortably fit a variety of different sized and shaped women and sufficient to function as described and claimed herein.

The flanged housing (205) further includes an upper receiving portion (215) having a first diameter (220). The first diameter (220) of the upper receiving portion being sized for receiving a portion of a breast and nipple of a user. In some embodiments, the first diameter (220) is approximately 3.5 inches, while in other embodiments the first diameter (220) may be greater than 3.5 inches or less than 3.5 inches for example. It being understood that the first diameter (220) may be any size and may be a variety of different sizes, to comfortably fit a variety of different sized and shaped women and sufficient to function as described and claimed herein.

Further, in some embodiments the angle of the upper receiving portion (215) Is approximately 105 degrees, while in other embodiments the angle of the upper receiving portion (215) may be greater than or less than 105 degrees. It being understood that the angle of the upper receiving portion (215) may be varied to fit a variety of different sized and different shaped women and to maximize user comfort. The upper receiving portion (215) may be detachably connected to the tubular middle portion (225) which may be detachably connected to the substantially tubular lower portion (235) in some embodiments. While in other embodiments, the upper receiving portion (215), tubular middle portion (225) and substantially tubular lower portion (235) may be formed from a single unitary piece of material, for example.

The flanged housing (205) further includes a substantially tubular middle portion (225) having a second diameter (230). In some embodiments the second diameter (230) of the middle portion (225) is approximately 1.310 inches, while in other embodiments the second diameter (230) may be greater than or less than 1.310 inches, for example. It being understood that the second diameter (230) may be varied to fit a variety of different sized and different shaped women and to maximize user comfort. Further, the upper receiving portion (215) may be detachably connected to the tubular middle portion (225) which may be detachably connected to the substantially tubular lower portion (235) in some embodiments. While in other embodiments, the upper receiving portion (215), tubular middle portion (225) and substantially tubular lower portion (235) may be formed from a single unitary piece of material, for example.

The second diameter (230) of the tubular middle portion (225) is less than the first diameter (220) of the upper receiving portion. The first diameter (220) of the upper receiving portion (215) being sized for receiving a portion of a breast and nipple of a user. As the first diameter (220) of the upper receiving portion (215) narrows at the mouth of the tubular middle portion (225), the upper receiving portion (215) fits directly over a user's breast and nipple to form a seal. The seal creates a vacuum that draws the nipple into the tubular middle portion (225) for milk extraction when the flange is connected to a breast pump.

The flanged housing (205) further includes a substantially tubular lower portion (235) having a third diameter (240). The third diameter (240) of the lower portion (235) is less than the first diameter (220) of the upper receiving portion and less than the second diameter (230) of the middle portion (225). The third diameter (240) of the lower portion (235) being sized for being detachably connected to a breast pump. The first diameter (220) of the upper receiving portion (215) narrows at the mouth of the tubular middle portion (225) and then the second diameter (230) narrows at the mouth of the lower portion (235) to create a seal. The seal creates a vacuum that draws the nipple into the tubular middle portion (225) for milk extraction when the flanged housing (205) is connected to a breast pump.

As described above, the flanged housing (205) may be constructed from a unitary piece of material or alternatively may be detachably connected from a variety of component parts. The flanged housing (205), including each of its component parts, may be constructed from any type of material that is sufficient to function as described and claimed herein. For example, the flanged housing (205) may be constructed from paper, plastics, nylon, silicone, metals, non-metals, alloys, resins, composite materials, organic compounds, non-organic compounds, fabrics, combinations thereof and the like. In some embodiments, the flanged housing (205) may have a thickness of approximately 0.050 inches. While in other embodiments, the flanged housing (205) may have a thickness greater than 0.050 inches, or in other embodiments the flanged housing (205) may have a thickness of less than 0.050 inches for example. However, the flanged housing (205) may be configured in a variety of dimensions to fit various sized and shaped breasts, including but not limited to configurations that are ergonomically designed to maximize comfort, for example.

Further in some embodiments, the flanged housing (205) may also include reinforcing or bracing structures such as struts, ribs, braces, rods or any other suitable reinforcing or bracing structure, or combinations thereof. The shape of the flanged housing (205) is shown as having a cone or circular shaped upper portion and a smaller funnel or tubular shaped middle portion (225) and lower portion (235). However, it should be understood, that the shape of the flanged housing (205) may be configured to have any desired shape, including but not limited to, a circular, triangular, square or any other desired shape sufficient to permit the flanged housing (205) to function as described herein.

Figure 3:
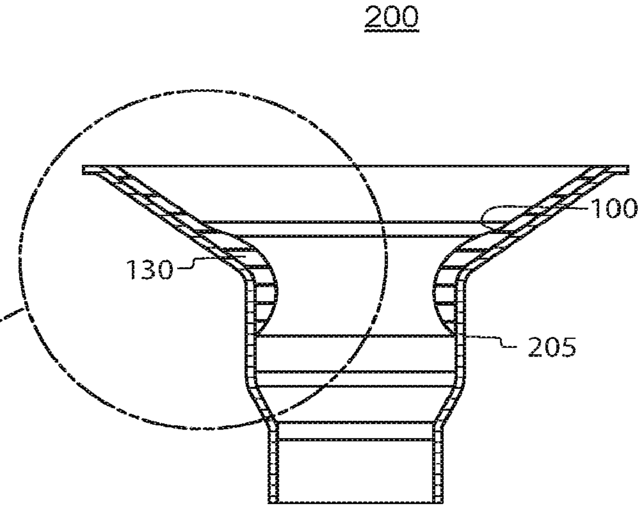
FIG. 3 is a side sectional view of an exemplary embodiment of a breast pump flange assembly (200) and flexible membrane (100) in accordance with the inventive concepts disclosed herein.
Figure 4:
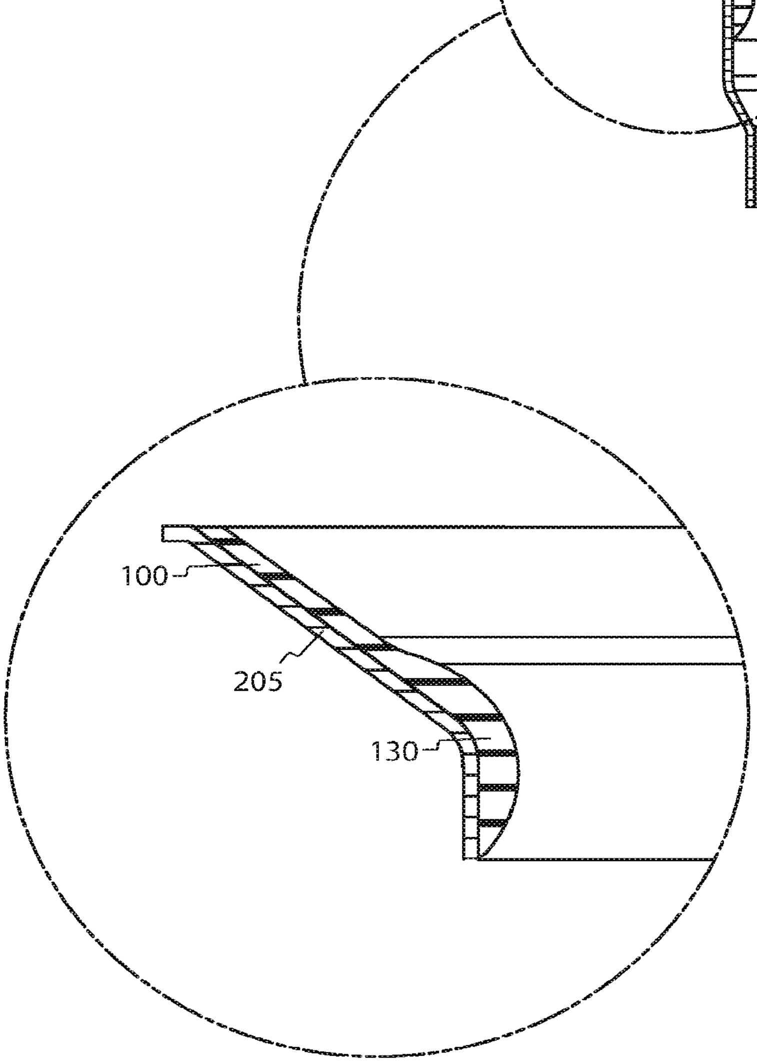
FIG. 4 is an exploded view of an exemplary embodiment of a support pad (130) of a breast pump flange assembly (200) in accordance with the inventive concepts disclosed herein.
Figure 5:
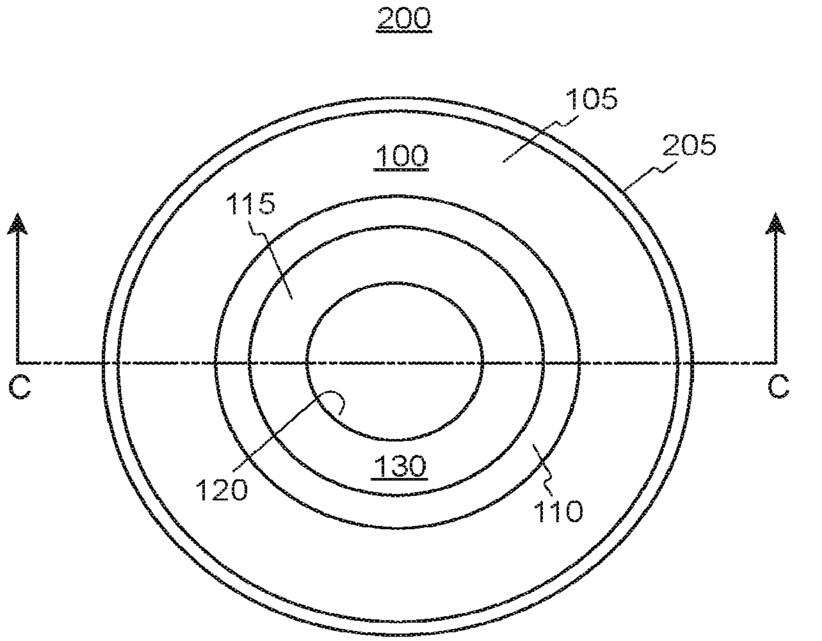
FIG. 5 is a top view of an exemplary embodiment of a breast pump flange assembly (200) and flexible membrane (100) in accordance with the inventive concepts disclosed herein.

Referring now to FIG. 3-5, shown therein is a breast pump flange assembly (200) in accordance with the inventive concepts disclosed and claimed herein. FIG. 3 depicts a side sectional view of an exemplary embodiment of a breast pump flange assembly (200) including a flexible membrane (100) in accordance with the inventive concepts disclosed herein. FIG. 4 depicts an exploded view of an exemplary embodiment of a support pad (130) of a breast pump flange assembly (200) in accordance with the inventive concepts disclosed herein. FIG. 5 depicts a top view of an exemplary embodiment of a breast pump flange assembly (200) and flexible membrane (100) in accordance with the inventive concepts disclosed herein.

As shown therein, the breast pump flange assembly (200) includes a flanged housing (205) having an interior chamber (210) extending therethrough. The flanged housing (205) having an upper receiving portion (215) having a first diameter (220), a substantially tubular middle portion (225) having a second diameter (230), and a substantially tubular lower portion (235) having a third diameter (240). The upper receiving portion (215) of the flanged housing (205) is configured for receiving a nipple of a user. The breast pump flange assembly (200) further includes a flexible membrane (100). The flexible membrane (100) including an outer portion (105), a middle portion (110), an inner portion (115), and an opening (120) extending therethrough. Wherein the inner portion (115) contains a support pad (130) positioned around the opening (120) of the flexible membrane (100). The support pad (130) configured to simulate the sensation of a baby's mouth on a user's breast by causing the breast to be massaged by intermittent suction action produced by a breast pump (209). Wherein the support pad (130) applies pressure to the mammary ducts of the breast increasing user comfort and breast milk productivity.

The flanged housing (205) is shown as having an interior chamber (210) extending therethrough. The interior chamber (210) of the flanged housing (205) is configured for receiving a nipple of a user and permitting breast milk to flow therethrough. In some embodiments, the interior chamber (210) has a diameter of approximately 3.336 inches at the mouth of the upper receiving portion (215), which narrows to a diameter of approximately 1.310 inches at the mouth of the tubular middle portion (225), which narrows to a diameter of approximately 1.00 inch at the mouth of the substantially tubular lower portion (235). It should be understood however, that the diameter of the interior chamber (210) may be any size and may be a variety of different sizes, to comfortably fit a variety of different sized and shaped women and sufficient to function as described and claimed herein.

The flanged housing (205) further includes an upper receiving portion (215) having a first diameter (220). The first diameter (220) of the upper receiving portion being sized for receiving a portion of a breast and nipple of a user. In some embodiments, the first diameter (220) is approximately 3.5 inches, while in other embodiments the first diameter (220) may be greater than 3.5 Inches or less than 3.5 inches for example. It being understood that the first diameter (220) may be any size and may be a variety of different sizes, to comfortably fit a variety of different sized and shaped women and sufficient to function as described and claimed herein.

Further, in some embodiments the angle of the upper receiving portion (215) is approximately 105 degrees, while in other embodiments the angle of the upper receiving portion (215) may be greater than or less than 105 degrees. It being understood that the angle of the upper receiving portion (215) may be varied to fit a variety of different sized and different shaped women and to maximize user comfort. The upper receiving portion (215) may be detachably connected to the tubular middle portion (225) which may be detachably connected to the substantially tubular lower portion (235) in some embodiments. While in other embodiments, the upper receiving portion (215), tubular middle portion (225) and substantially tubular lower portion (235) may be formed from a single unitary piece of material, for example.

The flanged housing (205) further includes a substantially tubular middle portion (225) having a second diameter (230). In some embodiments the second diameter (230) of the middle portion (225) is approximately 1.310 inches, while in other embodiments the second diameter (230) may be greater than or less than 1.310 inches, for example. It being understood that the second diameter (230) may be varied to fit a variety of different sized and different shaped women and to maximize user comfort. Further, the upper receiving portion (215) may be detachably connected to the tubular middle portion (225) which may be detachably connected to the substantially tubular lower portion (235) in some embodiments. While in other embodiments, the upper receiving portion (215), tubular middle portion (225) and substantially tubular lower portion (235) may be formed from a single unitary piece of material, for example.

The second diameter (230) of the tubular middle portion (225) is less than the first diameter (220) of the upper receiving portion. The first diameter (220) of the upper receiving portion (215) being sized for receiving a portion of a breast and nipple of a user. As the first diameter (220) of the upper receiving portion (215) narrows at the mouth of the tubular middle portion (225), the upper receiving portion (215) fits directly over a user's breast and nipple to form a seal. The seal creates a vacuum that draws the nipple into the tubular middle portion (225) for milk extraction when the flange is connected to a breast pump.

The flanged housing (205) further includes a substantially tubular lower portion (235) having a third diameter (240). The third diameter (240) of the lower portion (235) is less than the first diameter (220) of the upper receiving portion and less than the second diameter (230) of the middle portion (225). The third diameter (240) of the lower portion (235) being sized for being detachably connected to a breast pump. The first diameter (220) of the upper receiving portion (215) narrows at the mouth of the tubular middle portion (225) and then the second diameter (230) narrows at the mouth of the lower portion (235) to create a seal. The seal creates a vacuum that draws the nipple into the tubular middle portion (225) for milk extraction when the flanged housing (205) is connected to a breast pump.

As described above, the flanged housing (205) may be constructed from a unitary piece of material or alternatively may be detachably connected from a variety of component parts. The flanged housing (205), including each of its component parts, may be constructed from any type of material that is sufficient to function as described and claimed herein. For example, the flanged housing (205) may be constructed from paper, plastics, nylon, silicone, metals, non-metals, alloys, resins, composite materials, organic compounds, non-organic compounds, fabrics, combinations thereof and the like. In some embodiments, the flanged housing (205) may have a thickness of approximately 0.050 inches. While in other embodiments, the flanged housing (205) may have a thickness greater than 0.050 inches, or in other embodiments the flanged housing (205) may have a thickness of less than 0.050 inches for example. However, the flanged housing (205) may be configured in a variety of dimensions to fit various sized and shaped breasts, including but not limited to configurations that are ergonomically designed to maximize comfort, for example.

Further in some embodiments, the flanged housing (205) may also include reinforcing or bracing structures such as struts, ribs, braces, rods or any other suitable reinforcing or bracing structure, or combinations thereof. The shape of the flanged housing (205) is shown as having a cone or circular shaped upper portion and a smaller funnel or tubular shaped middle portion (225) and lower portion (235). However, it should be understood, that the shape of the flanged housing (205) may be configured to have any desired shape, including but not limited to, a circular, triangular, square or any other desired shape sufficient to permit the flanged housing (205) to function as described herein.

The breast pump flange assembly (200) further including a flexible membrane (100). The flexible membrane (100) including an outer portion (105), a middle portion (110), an inner portion (115), and an opening (120) extending therethrough. Wherein the inner portion (115) contains a support pad (130) positioned around the opening (120) of the flexible membrane (100). The support pad (130) configured to simulate the sensation of a baby's mouth on a user's breast by causing the breast to be massaged by intermittent suction action produced by a breast pump (209). Wherein the support pad (130) applies pressure to the mammary ducts of the breast increasing user comfort and breast milk productivity.

The support pad (130) may be any size or shape. For example, the support pad (130) may be substantially circular, square, triangular or any other desired shape. Each support pad (130) is configured to be modifiable in that each support pad (130) can be selectively connected, attached, or detached to or from the flexible membrane (100), in any number of positions, configurations or orientations on the flexible membrane (100), by the user at home on the fly and in real time, to create any number of custom fits and/or so that each support pad (130) can be selectively removed, washed, and then selectively reconnected or attached to the flexible membrane (100) for further use as desired. For example, a user may selectively attach one support pad (130) to the flexible membrane (100), and later desire to change the fit and add a second or third support pad (130) to the flexible membrane (100), or the user may rearrange the location or position of one of the support pad (130) connected to the flexible membrane (100) for additional or different support and comfort. Each support pad (130) may be selectively attached, connected, and detached to the flexible membrane (100) by a user by any connection means known in the art, including but not limited to, adhesives, including pressure and heat sensitive adhesives, chemical bonding, latches, structural grooves, ridges, ribs, locking mechanisms, pins, bolts, screws, flanges, and other connecting means known in the art. In some embodiments, the flexible membrane (100) may have no support pad (130), while in other embodiments, the flexible membrane (100) may have a plurality of support pad (130) connected thereto, for example. The position, configuration, and orientation of the support pad (130) on the flexible membrane (100) is capable of being rearranged and detachably connected and removed from the flexible membrane (100), in any orientation or position, for maximum comfort and so that the support pad (130) and the flexible membrane (100) may be used with a variety of different sized and shaped women without having to purchase more or different sized or shaped breast pump equipment. Thereby, providing significant advantages over traditional breast pump equipment.

The flexible membrane (100) may be detachably connected to the breast pump flange assembly (200) by any means known in the art, including but not limited to, an adhesive, a pressure sensitive adhesive, a clasp, screw, latch, locking mechanism, combinations thereof and the like, for example. Further, the support pad (130) may be detachably connected to the flexible membrane (100) by any means known in the art, including but limited to an adhesive, a pressure sensitive adhesive, a clasp, screw, latch, locking mechanism, combinations thereof and the like for example. The flexible membrane (100) and the support pad (130) may be formed from paper, plastic, hydrophobic polytetrafluoroethylene (PTFE), polymers, polypropylene, biaxial oriented polypropylene (BOPP) film, thermoplastic polymers, vinyl, such as static cling vinyl, opaque vinyl, clear vinyl, clear polyester, combinations thereof and the like. The flexible membrane (100) and support pad (130) may be non-porous or semi-porous so as to prevent or permit liquids and gases to or from passing through the flexible membrane (100) and the support pad (130); provided however, that any pores in the flexible membrane (100) and support pad (130) must be configured to substantially prevent liquids, such as breast milk, from passing through the flexible membrane (100) and support pad (130) during normal use. In some embodiments, the flexible membrane (100) and support pad (130) may also have reinforcement or lamination, including reinforcement or lamination to add durability, for example.

In some embodiments, the bottom side of the flexible membrane (100) and the bottom side of the support pad (130) is coated with a pressure sensitive adhesive. The pressure sensitive adhesive may be a coating or thin layer of adhesive material sufficient to permit the flexible membrane (100) to stick to the interior of the flanged housing (205) and to permit the support pad (130) to stick to the top side of the flexible membrane (100). The adhesive material may be a non-reactive adhesive which forms a bond when pressure is applied to bond the adhesive with the adherend. No solvent, water or heat is needed to activate the adhesive for a pressure sensitive adhesive. However, it should be understood to one of ordinary skill in the art that other types of adhesives may be used with the flexible membrane (100) and support pad (130), including, for example, structural, chemical or heat adhesives and the like.

The degree of the bond for the pressure sensitive adhesive may be influenced by the amount of pressure which is used to apply the pressure sensitive adhesive to the surface. Surface factors such as smoothness, surface energy, and removal of contaminants are also important to create proper bonding. As will be appreciated by one of ordinary skill in the art, pressure sensitive adhesives are generally designed with a balance between flow and resistance to flow. The bond forms because the adhesive is soft enough to flow, or wet, the adherend. The bond has strength because the adhesive is hard enough to resist flow when stress is applied to the bond. Once the adhesive and the adherend are in proximity, there are also molecular interactions such as van der Waals forces involved in the bond, which contribute significantly to the ultimate bond strength.

Because some pressure sensitive adhesives reduce their shear holding ability at low or high temperatures (temperatures significantly above or below standard room temperature of 73.4 degrees Fahrenheit), the pressure sensitive adhesive may be configured to retain its bond during use at elevated temperatures. The pressure sensitive adhesive may also exhibit viscoelastic (viscous and elastic) properties, both of which are used for proper bonding, for example.

The pressure sensitive adhesive may be constructed with either a liquid carrier or in solid form. The pressure sensitive adhesive may be made from liquid pressure sensitive adhesives by coating the adhesive on a support and evaporating the organic solvent or water carrier, usually in a hot air dryer, for example. The dry adhesive may be further heated to initiate a cross-linking reaction and increase molecular weight. Solid pressure sensitive adhesives may be low viscosity polymers that are coated and then reacted with radiation to increase molecular weight and form the adhesive (radiation cured pressure sensitive adhesives); or they may be high-viscosity materials that are heated to reduce viscosity enough to allow coating, and then cooled to their final form (hot melt pressure sensitive adhesives).

The pressure sensitive adhesive may be based on an elastomer compounded with a suitable tackifier (e.g., a rosin ester). The elastomers can be based on acrylics, which can have sufficient tack on their own and may not require a tackifier; bio-based acrylate, butyl rubber, ethylene-vinyl acetate (EVA) with high vinyl acetate content; can be formulated as a hot-melt pressure sensitive adhesive, natural rubber, nitriles, silicone rubbers, requiring special tackifiers based on “MQ” silicate resins, composed of a monofunctional trimethyl silane (“M”) reacted with quadrafunctional silicon tetrachloride (“Q”).

Further, the pressure sensitive adhesive may include styrene block copolymers (SBC), also called styrene copolymer adhesives and rubber-based adhesives, which have good low-temperature flexibility, high elongation, and high heat resistance. Such compounds may have an A-B-A structure, including an elastic rubber segment between two rigid plastic endblocks; high-strength film formers which increase cohesion and viscosity as an additive; and may be water-resistant, with cross-linking to improve solvent resistance. Resins associating to the end blocks (cumarone-indene, $\alpha$-methyl styrene, vinyl toluene, aromatic hydrocarbons, etc.) improve adhesion and alter viscosity. Resins associating to the mid blocks (aliphatic olefins, rosin esters, polyterpenes, terpene phenolics) also improve adhesion, processing and pressure-sensitive properties. The addition of plasticizers reduces cost, improves pressure-sensitive tack, decrease melt viscosity, decreases hardness, and improves low-temperature flexibility. The A-B-A structure promotes a phase separation of the polymer, binding together the end blocks, with the central elastic parts acting as cross-links; SBCs may also include additional cross-linking, styrene-butadiene-styrene (SBS), which may be used in high-strength pressure sensitive adhesive applications or styrene-ethylene/butylene-styrene (SEBS), used in low self-adhering non-woven applications, or styrene-ethylene/propylene (SEP) and styrene-isoprene-styrene (SIS), used in low-viscosity high-tack pressure sensitive adhesive applications, including vinyl ethers, for example.

The flexible membrane (100) and support pad (130) may be constructed from a unitary piece of material or alternatively may be constructed from a variety of component parts and detachably connected, for example. The flexible membrane (100), including each of its component parts, such as the support pad (130) for example, if any, may be constructed from any type of material that is sufficient to function as described and claimed herein. For example, the flexible membrane (100) and support pad (130) may be constructed from paper, plastics, nylon, silicone, hydrophobic polytetrafluoroethylene (PTFE), polymers, polypropylene, biaxial oriented polypropylene (BOPP) film, thermoplastic polymers, vinyl, such as static cling vinyl, opaque vinyl, clear vinyl, clear polyester polymers, metals, non-metals, alloys, resins, composite materials, organic compounds, non-organic compounds, fabrics, combinations thereof and the like.

Further, in some embodiments, the flexible membrane (100) and support pad (130) may also include reinforcing or bracing structures such as struts, ribs, braces, rods or any other suitable reinforcing or bracing structure, or combinations thereof. The shape of the flexible membrane (100) and support pad (130) is shown as having a conical or circular shape. However, it should be understood, that the shape of the flexible membrane (100), support pad (130), and flanged housing (205) may be configured to have any desired shape, including but not limited to, a rectangular, triangular, square or any other desired shape sufficient to permit the flexible membrane (100) and support pad (130) to function as described herein.

The flexible membrane (100) includes an outer portion (105), a middle portion (110), an inner portion (115), and an opening (120) extending therethrough. Wherein the inner portion (115) contains a support pad (130) positioned around the opening (120) of the flexible membrane (100). In some embodiments, the flexible membrane (100) may have a thickness of approximately 0.03 inches. While in other embodiments, the flexible membrane (100) may have a thickness greater than 0.03 inches, or in other embodiments the flexible membrane (100) may have a thickness of less than 0.03 inches for example. However, the flexible membrane (100) and each support pad (130) may be configured in a variety of dimensions to fit various sized and shaped breasts, including but not limited to configurations that are ergonomically designed to maximize comfort, for example.

The outer portion (105) may have a thickness of approximately 0.03 inches and is configured to rest within or be detachably connected to the upper receiving portion (215) of the flanged housing (205). As discussed above, however, the thickness of the outer portion (105) may be greater or less than 0.03 inches in some embodiments to fit various sized and shaped breasts. Similarly, the middle portion (110) may also have a thickness of approximately 0.03 inches and may be configured to rest within or be detachably connected to the middle portion (225) of the flanged housing (205). As discussed above, however, the thickness of the outer portion (105) may be greater or less than 0.03 inches in some embodiments to fit various sized and shaped breasts. The inner portion (115) may also have a thickness of approximately 0.03 inches and may be configured to rest within or be detachably connected to the middle portion (225) of the flanged housing (205).

As discussed above, however, the inner portion (115) may be greater or less than 0.03 inches in some embodiments to fit various sized and shaped breasts. At the center of the flexible membrane (100) is an opening (120) extending therethrough. The opening (120) having a diameter of approximately 1.060 inches. It being understood, however, that the opening (120) may have a diameter greater or less than 1.060 inches, in certain embodiments, to fit various sized and shaped breasts. The opening (120) configured to receiving a nipple therethrough.

Surrounding the opening (120) of the flexible membrane (100) is the support pad (130). The support pad (130) is configured to simulate the sensation of a baby's mouth on a user's breast by causing the breast to be massaged by intermittent suction action produced by a breast pump (209). Wherein the support pad (130) applies pressure to the mammary ducts of the breast increasing user comfort and breast milk productivity. In some embodiments, the support pad (130) may have a thickness of approximately 0.25 inches. While in other embodiments, the support pad (130) may have a thickness greater than 0.25 inches, or in other embodiments the support pad (130) may have a thickness of less than 0.25 inches for example. However, the support pad (130) may be configured in a variety of dimensions to fit various sized and shaped breasts, including but not limited to configurations that are ergonomically designed to maximize comfort, for example.

The support pad (130) provides a flexible pillow that is positioned around the opening (120) of the funnel where the seal is typically formed. The configuration, position and number of support pad (130) may be modified, increased or decreased to accommodate a variety of different sized and shaped women and to provide maximum comfort and versatility. For example, each support pad (130) is configured to be modifiable in that they can each be selectively connected, attached, or detached to or from the flexible membrane (100), in any number of positions, configurations or orientations on the flexible membrane (100), by the user at home on the fly and in real time, to create any number of custom fits and/or so that each support pad (130) can be selectively removed, washed, and then selectively reconnected or attached to the flexible membrane (100) for further use as desired. For example, a user may selectively attach one support pad (130) to the flexible membrane, and later desire to change the fit and add a second or third support pad (130) to the flexible membrane (100), or the user may rearrange the location or position of each of the support pad (130) connected to the flexible membrane (100) for additional or different support and comfort. Each support pad (130) may be selectively attached, connected, and detached to the flexible membrane (100) by a user by any connection means known in the art, including but not limited to, adhesives, including pressure and heat sensitive adhesives, chemical bonding, latches, structural grooves, ridges, ribs, locking mechanisms, pins, bolts, screws, flanges, and other connecting means known in the art. In some embodiments, the flexible membrane (100) may have no support pad (130), while in other embodiments, the flexible membrane (100) may have one, two or more support pad (130) connected thereto, for example. The position, configuration, and orientation of each of the support pad (130) on the flexible membrane (100) are capable of being rearranged and detachably connected and removed from the flexible membrane (100), in any orientation or position, for maximum comfort and so that the support pad (130) and the flexible membrane (100) may be used with a variety of different sized and shaped women without having to purchase more or different sized or shaped traditional breast pump equipment. Thereby, providing significant advantages over traditional breast pump equipment. In some embodiments, the support pad (130) is filled with a movable substance, such as a liquid or gel. For example, compositions containing water, silicone, polymers, or plastics for example. While in other embodiments, the support pad (130) may be constructed from or contain solid or semi-solid materials, including silicone, plastics, rubber, plastics and the like for example. The support pad is configured to simulate the movement and sensation of a baby's mouth on a breast, causing the breast to be massaged by the intermittent suction action produced when the flange assembly (200) is attached to a breast pump. The massaging pressure produced by the support pad (130) which is applied to the mammary ducts of the breast significantly increases user comfort, health and breast milk productivity. Thus, providing significant advantages over traditional breast pump flanges and breast shields. The support pad (130) provides soft contact around the circumference of the areola to the nipple, applying consistent pressure to the mammary ducts of the breast. Utilizing the intermittent suction action of the breast pump, the support pad (130) causes the nipple to be massaged during the suction process creating a more natural sensation (like a baby sucking) on the breast. This facilitates breast feeding by increasing comfort and productivity in producing breast milk while pumping.

Figure 6:
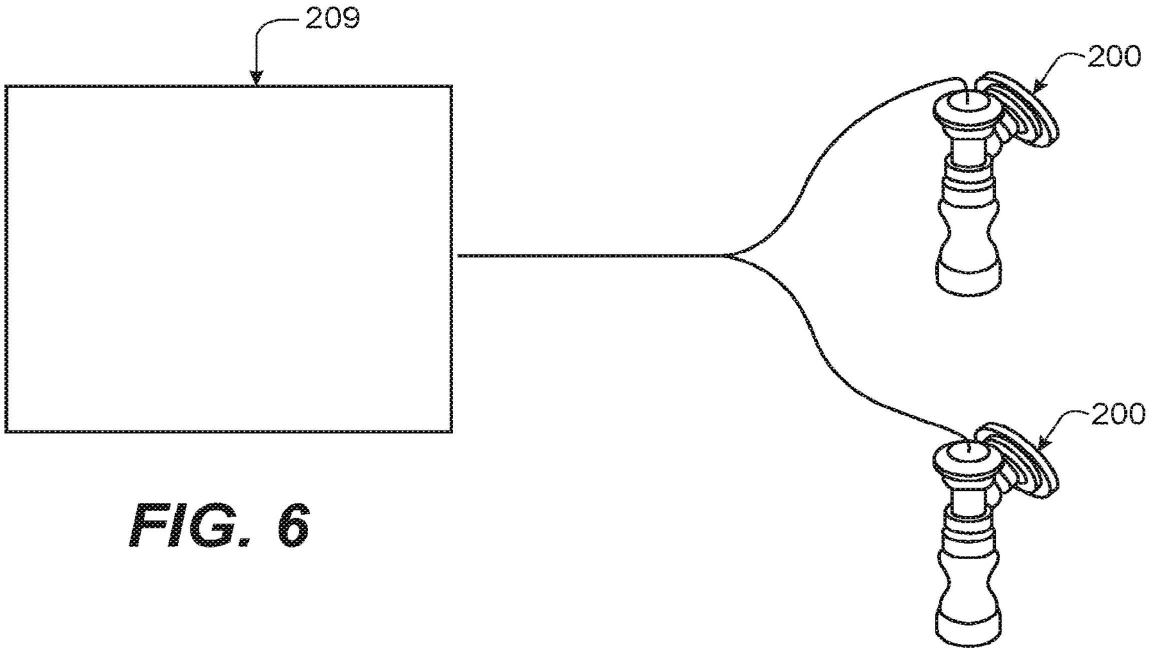
FIG. 6 is a perspective view of an exemplary embodiment of a breast pump (209) detachably connected to a breast pump flange assembly (200) in accordance with the inventive concepts disclosed herein.

Referring now to FIG. 6, shown therein is a perspective view of an exemplary embodiment of a breast pump (209)

detachably connected to a breast pump flange assembly (200) in accordance with the inventive concepts disclosed herein. The breast pump flange assembly (200) includes a flanged housing (205) having an interior chamber (210) extending therethrough. The flanged housing (205) having an upper receiving portion (215) having a first diameter (220), a substantially tubular middle portion (225) having a second diameter (230), and a substantially tubular lower portion (235) having a third diameter (240). The upper receiving portion (215) of the flanged housing (205) is configured for receiving a nipple of a user. The breast pump flange assembly (200) further including a flexible membrane (100). The flexible membrane (100) including an outer portion (105), a middle portion (110), an inner portion (115), and an opening (120) extending therethrough.

Wherein the inner portion (115) contains a support pad (130) positioned around the opening (120) of the flexible membrane (100). The support pad (130) configured to simulate the sensation of a baby's mouth on a user's breast by causing the breast to be massaged by intermittent suction action produced by a breast pump (209). Wherein the support pad (130) applies pressure to the mammary ducts of the breast increasing user comfort and breast milk productivity.

Figure 7:
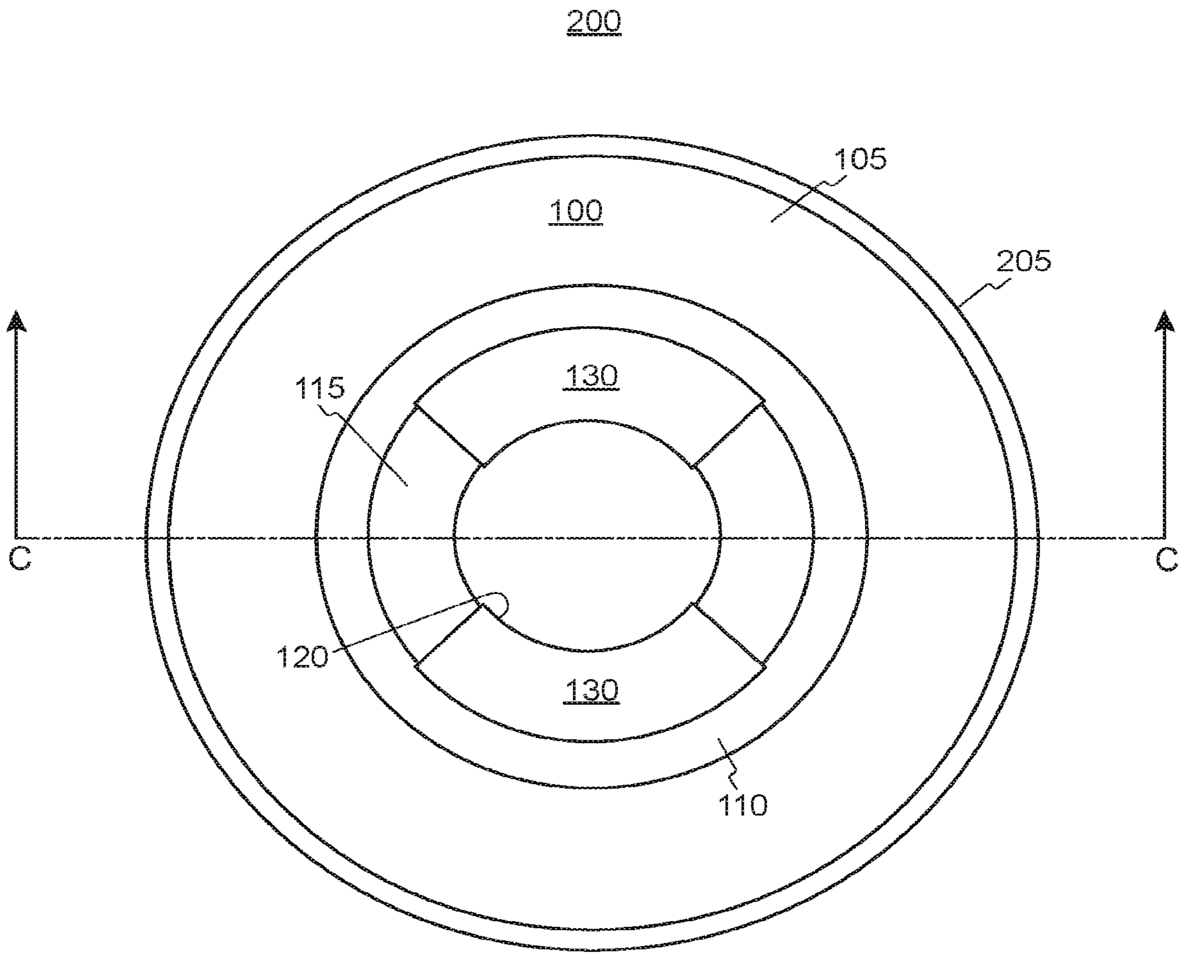
FIG. 7 is a top view of an embodiment of a breast pump flange assembly (200) and flexible membrane (100) in accordance with the inventive concepts disclosed herein.

Referring now to FIG. 7, shown therein is an embodiment of the breast pump flange assembly (200). The breast pump flange assembly (200) includes a flanged housing (205) having an interior chamber (210) extending therethrough. The flanged housing (205) having an upper receiving portion (215) having a first diameter (220), a substantially tubular middle portion (225) having a second diameter (230), and a substantially tubular lower portion (235) having a third diameter (240). The upper receiving portion (215) of the flanged housing (205) is configured for receiving a nipple of a user.

The breast pump flange assembly (200) further includes a flexible membrane (100). The flexible membrane (100) including an outer portion (105), a middle portion (110), an inner portion (115), and an opening (120) extending therethrough. Wherein the inner portion (115) contains one or more support pad (130) positioned at least partially around the opening (120) of the flexible membrane (100). The one or more support pad (130) configured to simulate the sensation of a baby's mouth on a user's breast by causing the breast to be massaged by intermittent suction action produced by a breast pump (209). Wherein the one or more support pad (130) applies pressure to the mammary ducts of the breast increasing user comfort and breast milk productivity.

Each support pad (130) provides a flexible pillow that is positioned at least partially around the opening (120) of the funnel where the seal is typically formed. Each support pad (130) may be any size or shape. For example, the support pad (130) may be substantially circular, rectangular, square or triangular in shape. Further, the configuration, position and number of each support pad (130) may be modified, increased or decreased to accommodate a variety of different sized and shaped women and to provide maximum comfort and versatility. For example, each support pad (130) is configured to be modifiable in that they can each be selectively connected, attached, or detached to or from the flexible membrane (100), in any number of positions, configurations or orientations on the flexible membrane (100), by the user at home on the fly and in real time, to create any number of custom fits and/or so that each support pad (130) can be selectively removed, washed, and then selectively reconnected or attached to the flexible membrane (100) for further use as desired. For example, a user may selectively attach one support pad (130) to the flexible membrane (100), and later desire to change the fit and add a second or third support pad (130) to the flexible membrane (100), or the user may rearrange the location or position of each support pad (130) connected to the flexible membrane (100) for additional or different support and comfort. Each support pad (130) may be selectively attached, connected, and detached to the flexible membrane (100) by a user by any connection means known in the art, including but not limited to, adhesives, including pressure and heat sensitive adhesives, chemical bonding, latches, structural grooves, ridges, ribs, locking mechanisms, pins, bolts, screws, flanges, and other connecting means known in the art. In some embodiments, the flexible membrane (100) may have no support pad (130), while in other embodiments, the flexible membrane (100) may have one, two, three or more support pad (130) connected thereto, for example. The position, configuration, and orientation of each support pad (130) attached to the flexible membrane (100) are capable of being rearranged and detachably connected and removed from the flexible membrane (100), in any orientation or position, for maximum comfort and so that each of the support pad (130) and the flexible membrane (100) may be used with a variety of different sized and shaped women without having to purchase more or different sized or shaped traditional breast pump equipment. Thereby, providing significant advantages over traditional breast pump equipment. In some embodiments, each support pad (130) is filled with a movable substance, such as a liquid or gel. For example, compositions containing water, silicone, polymers, or plastics for example. While in other embodiments, each support pad (130) may be constructed from or contain solid or semi-solid materials, including silicone, plastics, rubber, plastics and the like for example. Each support pad is configured to simulate the movement and sensation of a baby's mouth on a breast, causing the breast to be massaged by the intermittent suction action produced when the flange assembly (200) is attached to a breast pump. The massaging pressure produced by each of the support pad (130) which is applied to the mammary ducts of the breast significantly increases user comfort, health and breast milk productivity. Thus, providing significant advantages over traditional breast pump flanges and breast shields. Each support pad (130) provides soft contact at least partially around the circumference of the areola to the nipple, applying pressure to the mammary ducts of the breast. Utilizing the intermittent suction action of the breast pump, each support pad (130) causes the nipple to be massaged during the suction process creating a more natural sensation (like a baby sucking) on the breast. This facilitates breast feeding by increasing comfort and productivity in producing breast milk while pumping.

In some embodiments the support pad (130) is positioned completely around the opening (120), while in other embodiments, the support pad (130) may be positioned partially around the opening (120), while in other embodiments there may be more than one support pad (130) (as shown in FIG. 7), with each support pad (130) positioned at a different location around the opening (120). For example, in some embodiments, one support pad (130) may be positioned around an upper portion of the opening (120) while a second support pad (130) may be positioned around a lower portion of the opening (120) (as shown in FIG. 7). In this embodiment, no support pad (130) is found around the sides of the opening (120), so as to mimic the sensation of a baby's mouth on a user's breast. The configuration, position and number of support pad (130) may be modified, increased or decreased to accommodate a variety of different sized and shaped women and to provide maximum comfort and versatility. For example, each support pad (130) is configured to be modifiable in that they can each be selectively connected, attached, or detached to or from the flexible membrane (100), in any number of positions, configurations or orientations on the flexible membrane (100), by the user at home on the fly and in real time, to create any number of custom fits and/or so that each support pad (130) can be selectively removed, washed, and then selectively reconnected or attached to the flexible membrane for further use as desired. For example, a user may selectively attach one support pad (130) to the flexible membrane (100), and later desire to change the fit and add a second or third support pad (130) to the flexible membrane (100), or the user may rearrange the location or position of each support pad (130) attached to the flexible membrane (100) for additional or different positioned support and comfort. Each support pad (130) may be selectively attached, connected, and detached to the flexible membrane (100) by a user by any connection means known in the art, including but not limited to, adhesives, including pressure and heat sensitive adhesives, chemical bonding, latches, structural grooves, ridges, ribs, locking mechanisms, pins, bolts, screws, flanges, and other connecting means known in the art. In some embodiments, the flexible membrane (100) may have no support pad (130) attached thereto, while in other embodiments, the flexible membrane (100) may have one, two, three or more support pad (130) connected thereto, for example. The position, configuration, and orientation of each support pad (130) on the flexible membrane (100) is capable of being rearranged and detachably connected and removed from the flexible membrane (100), in any orientation or position, for maximum comfort and so that the support pad (130) and the flexible membrane (100) may be used with a variety of different sized and shaped women without having to purchase more or different sized or shaped traditional breast pump equipment. Thereby, providing significant advantages over traditional breast pump equipment.

It is to be appreciated that embodiments of the breast pump flange assembly (200), flexible membrane (100), and support pad (130) may be used under a variety of different conditions and with a variety of different breast pumps and breast pump flanges and breast shields, for example. Further, embodiments of the breast pump flange assembly (200), flexible membrane (100) and support pad (130) may be shipped fully assembled, fully or partially disassembled as will be readily appreciated by persons of ordinary skill in the art.

From the above description, it is clear that the inventive concepts disclosed herein are adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the broad scope of the inventive concepts disclosed herein and defined by the appended claims.

What is claimed is:

1. A flexible membrane constructed from silicone configured for insertion into a breast pump flanged housing, the flexible membrane comprising: an outer portion, a middle portion, an inner portion, and an opening extending therethrough, wherein the inner portion contains a plurality of support pads that are each detachably connected to the flexible membrane, each support pad positioned partially around the opening of the flexible membrane in a configuration to mimic the feel of a baby's mouth on a breast, the plurality of support pads each having a separate internal chamber containing silicone, the plurality of support pads configured to simulate the sensation of a baby's mouth on the user's breast when the flexible membrane is inserted into the breast pump flanged housing and used with a breast pump, the plurality of support pads positioned around the opening of the flexible membrane are configured to cause the breast to be massaged by each of the support pads by intermittent suction action produced by the breast pump; wherein the plurality of support pads are configured to apply pressure to the mammary ducts of the breast thereby increasing user comfort and breast milk productivity.

2. The flexible membrane of claim 1 wherein each support pad contains a liquid.

3. The flexible membrane of claim 1 wherein each support pad contains a gel.

4. The flexible membrane of claim 1 further comprising reinforcement for strength and durability.

5. The flexible membrane of claim 1 wherein each support pad further comprises a pressure sensitive adhesive on a bottom portion of the support pad configured to be detachably connected to the flexible membrane such that each support pad may be selectively attached and selectively positioned to the flexible membrane in a desired configuration to mimic the feel of the baby's mouth on the breast and for comfort for different sized and shaped users.

6. A breast pump flange assembly comprising:

a flanged housing constructed from nylon, the flanged housing having an interior chamber extending therethrough, the flanged housing having an upper receiving portion having a first diameter, a substantially tubular middle portion having a second diameter, and a substantially tubular lower portion having a third diameter, the upper receiving portion of the flanged housing configured for receiving a nipple of a user; and a flexible membrane constructed from silicone, the flexible membrane detachably connected to the flanged housing, the flexible membrane comprising: an outer portion, a middle portion, an inner portion, and an opening extending therethrough, wherein the inner portion contains a plurality of support pads that are each detachably connected to the flexible membrane, each support pad positioned around the opening of the flexible membrane in a configuration to mimic the feel of a baby's mouth on a breast, the plurality of support pads each having a separate internal chamber containing silicone, the plurality of support pads configured to simulate the sensation of the baby's mouth on the user's breast by causing the breast to be massaged by each of the support pads by intermittent suction action produced by a breast pump; wherein the support pads are configured to apply pressure to the mammary ducts of the breast thereby increasing user comfort and breast milk productivity.

7. The breast pump flange assembly of claim 6 wherein the flexible membrane further comprises reinforcement for strength and durability.

8. The breast pump flange assembly of claim 6 wherein each support pad of the flexible membrane further comprises a pressure sensitive adhesive on a bottom portion of the support pad configured to be detachably connected to the flexible membrane such that each support pad may be selectively attached and positioned to the flexible membrane in a desired configuration to mimic the feel of the baby's mouth on the breast and for comfort for different sized and shaped users.

* * * * *